United States Patent
Brazdil et al.

(10) Patent No.: US 11,578,048 B2
(45) Date of Patent: Feb. 14, 2023

(54) DEHYDRATION AND CYCLIZATION OF α-, β-DIHYDROXY CARBONYL COMPOUNDS TO 2-SUBSTITUTED FURAN DERIVATIVES

(71) Applicant: Archer Daniels Midland Company, Decatur, IL (US)

(72) Inventors: James Brazdil, Glen Ellyn, IL (US); Donald Rogness, Del Mar, CA (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 0 days.

(21) Appl. No.: 17/046,754

(22) PCT Filed: Apr. 4, 2019

(86) PCT No.: PCT/US2019/025785
§ 371 (c)(1),
(2) Date: Oct. 9, 2020

(87) PCT Pub. No.: WO2019/199570
PCT Pub. Date: Oct. 17, 2019

(65) Prior Publication Data
US 2021/0163436 A1 Jun. 3, 2021

Related U.S. Application Data

(60) Provisional application No. 62/657,416, filed on Apr. 13, 2018.

(51) Int. Cl.
C07D 307/68 (2006.01)

(52) U.S. Cl.
CPC .................. *C07D 307/68* (2013.01)

(58) Field of Classification Search
CPC ...................................... C07D 307/68
USPC ........................................... 549/485
See application file for complete search history.

(56) References Cited

U.S. PATENT DOCUMENTS

2015/0336090 A1* 11/2015 Kanna .................... B01J 29/072
549/485

OTHER PUBLICATIONS

Noma et al, Formation of 5-(Hydroxymethyl)furfural by Stepwise Dehydration over TiO2 with Water-Tolerant Lewis Acid Sites, J. Phys. Chem. C 2015, 119, 17117-17125. (Year: 2015).*

(Continued)

*Primary Examiner* — Taylor V Oh
(74) *Attorney, Agent, or Firm* — William B. Miller

(57) ABSTRACT

Processes are disclosed for the synthesis of 2-substituted furan derivatives, such as furan dicarboxylic acid (FDCA), from a starting compound or substrate having a carbonyl functional group (C=O), with hydroxy-substituted carbon atoms at alpha (α) and beta (β) positions, relative to the carbonyl functional group. According a particular embodiment, an α-, β-dihydroxy carboxylate is dehydrated to form a dicarbonyl intermediate by transformation of the α-hydroxy group to a second carbonyl group and removal of the β-hydroxy group. The dicarbonyl intermediate undergoes cyclization and dehydration, to produce the 2-substituted furan derivative. Optionally, a further step of oxidation may be carried out, for example to convert a hydroxymethyl group, as a 5-substituted about the furan ring, to a carboxy group of FDCA.

17 Claims, 1 Drawing Sheet

(56) References Cited

OTHER PUBLICATIONS

Putten et al, Hydroxymethylfurfural, a Versatile Platform Chemical Made from Renewable Resources, Chem. Rev. 2013, 113, 1499-1597 (Year: 2013).*

* cited by examiner

DEHYDRATION AND CYCLIZATION OF α-, β-DIHYDROXY CARBONYL COMPOUNDS TO 2-SUBSTITUTED FURAN DERIVATIVES

CROSS-REFERENCE TO RELATED APPLICATIONS

This application is a national stage entry of International Application No. PCT/US19/25785, filed Apr. 4, 2019, which itself claims priority to U.S. Provisional Patent Application No. 62/657,416, filed Apr. 13, 2018, the contents of each are incorporated herein by reference.

FIELD OF THE INVENTION

The present invention relates to methods for synthesizing 2-substituted furan derivatives, including furandicarboxylic acid, from α-, β-dihydroxy carbonyl starting compounds, including α-, β-dihydroxy carboxylic acids and carboxylates, such as products obtained from glucose.

BACKGROUND OF THE INVENTION

The depletion of fossil fuels has created major incentives for seeking alternative sources to petroleum-based carbon for the synthesis of so-called "platform" molecules that can serve as the building blocks for commercially significant products. Biomass is currently viewed as a potential replacement from which many such high value chemicals can be derived, but the development of sustainable technologies for the production of such chemicals from renewable resources remains a significant challenge.

Furandicarboxylic acid (FDCA) is recognized as a bio-based monomer for the polymer known as polyethylene-furanonate (PEF), which is a substitute for, and in fact superior in a number of respects to, the petroleum derived commodity product polyethylene terephthalate (PET). FDCA is also a useful platform chemical in the production of polyamides, polyurethanes, and esters having diverse applications as plastics, fibers, coatings, adhesives, personal care products, and lubricants. In the case of PEF, this bio-plastic is particularly useful as a material for bottles and fibers, as well as films used to manufacture pouches, wrappers, and heat shrink materials. In the area of packaging, PEF can be blended with PET to provide a superior product in terms of barrier properties for $CO_2$ and $O_2$, leading to an improved shelf life over pure PET and providing an acceptable container for products such as beer which are susceptible to oxidative degradation. Other important characteristics of PEF relate to its high mechanical strength and recyclability.

Industrially important organic molecules such as FDCA are therefore seen as viable alternatives to their counterparts derived from conventional petroleum refining. The present state of the art would benefit significantly from synthesis pathways to such high value chemicals, from readily available or obtainable substrates.

SUMMARY

Aspects of the invention are associated with the discovery of synthesis methods that can utilize substrates such as gluconic acid and glucaric acid, which are readily derived, for example from the oxidation of glucose. Advantageously, in the case of such carboxylate (carboxylic acid) substrates or starting compounds, they may potentially exhibit greater stability compared to their precursor aldehydes (e.g., glucose). Under high temperature reaction conditions, this stability can lead to increased reaction selectivity and yield along a desired reaction sequence leading to the production of one or more defined products. Product losses due to undesired side reactions are thereby reduced. Products of particular interest include cyclized products and particularly furan derivatives that can be readily converted to furandicarboxylic acid (FDCA) and other molecules of interest. Obtaining suitable substrates from the oxidation of aldehyde precursors to carboxylates is straightforward and inexpensive, generally requiring only air as an oxidizing agent. Particular aspects are associated with the ability of the carboxylate anion-containing substrates, or their corresponding free acids, to undergo a series of reaction steps in solution, leading to the formation of desirable 2-substituted furan derivatives such as the 2,5-substituted product, 5-(hydroxymethyl)furan-2-carboxylic acid, which may be further converted under the same reaction conditions (e.g., by oxidation), advantageously in the same reactor (providing a "single pot" synthesis route) to FDCA.

Further aspects relate to synthesis pathways that utilize a cyclization step, following the formation of a dicarbonyl intermediate from a starting compound that may be characterized as an α-, β-dihydroxycarbonyl compound. The cyclization may be accompanied by a second dehydration to convert an initially-formed, saturated tetrahydrofuran ring to a furan ring. This second dehydration can be promoted using a suitable dehydration catalyst, under reaction conditions as described herein. More particular aspects relate to the discovery of such synthesis pathways, or individual reaction steps of such pathways, which may be performed non-enzymatically, meaning without the use of an enzyme (e.g., a polypeptide) in the reaction mixture. In the case of methods described herein being carried out non-enzymatically, such as using solely one or more chemical catalysts as opposed to biological catalyst(s), advantages reside in terms of allowing a wider range of possible reaction conditions, such as conditions of temperature and/or pH that would be detrimental to biological agents (e.g., would denature proteins including enzymes) but that nonetheless allow high productivities of a desired intermediate and/or end product. Other advantages may result from decreased operating costs, and particularly those otherwise associated with enzyme separation from the product, compared to the relatively lower costs associated with heterogeneous or homogeneous chemical catalyst separation. According to some embodiments, at least one of the synthesis steps described herein of (i) dehydrating the starting compound to form the dicarbonyl intermediate, (ii) cyclizing the dicarbonyl intermediate to produce the 2-substituted furan derivative or otherwise produce the 2-substituted tetrahydrofuran derivative, and (iii) dehydrating the 2-substituted tetrahydrofuran derivative to the 2-substituted tetrahydrofuran derivative, is a non-enzymatic reaction step (i.e., is not catalyzed using an enzyme). Preferably, at least two of (i), (ii), and (iii) are non-enzymatic reaction steps, and more preferably all of (i), (ii), and (iii) are non-enzymatic reaction steps.

Embodiments of the invention relate to methods for the synthesis of a 2-substituted furan derivative from a non-cyclic starting compound or substrate that includes a carbonyl functional group (C=O), with hydroxy-substituted carbon atoms at alpha (α) and beta (β) positions, relative to the carbonyl functional group. According to one reaction step, this starting compound, namely a non-cyclic α-, β-dihydroxy carbonyl compound selected from the group consisting of α-, β-dihydroxy carboxylates and carboxylic acids, is dehydrated to form a dicarbonyl intermediate by transformation of the α-hydroxy group to a second carbonyl group (adjacent a carbonyl group of the starting compound) and removal of the β-hydroxy group. The dicarbonyl intermediate then undergoes cyclization to form a 2-substituted furan derivative, optionally following dehydration of a corresponding 2-substituted tetrahydrofuran derivative. These derivatives may be more particularly 2,5-substituted compounds in which the 5-substituent of the furan or tetrahydrofuran ring corresponds to a portion of the substrate (e.g., a substituent of the delta carbon atom of this substrate) that does not cyclize.

The 2-substituted furan derivative, such as the 2,5-substituted furan derivative, may be oxidized in a separate reaction step to form an oxidized end product such as FDCA. Preferably, if such oxidation is performed, it is carried out in the same reactor and under the same conditions as used to synthesize the 2-substituted furan derivative.

These and other aspects, embodiments, and associated advantages will become apparent from the following Detailed Description.

Figure 1:
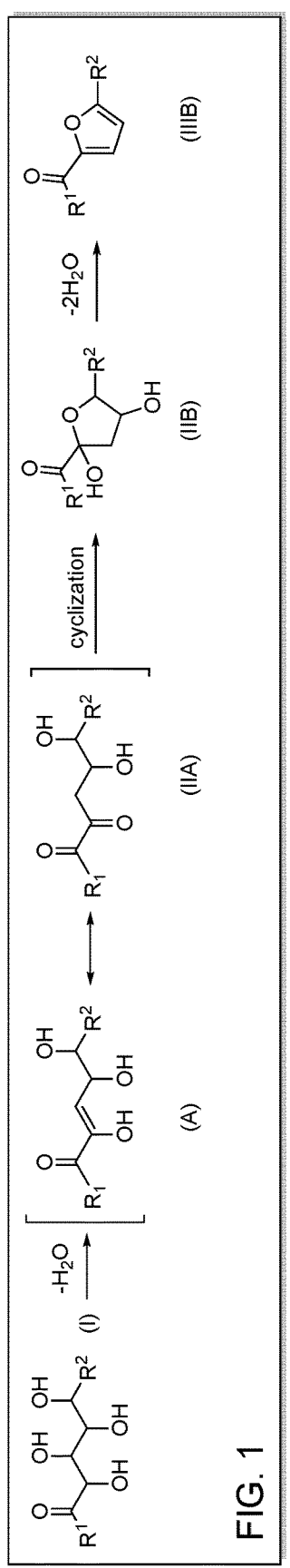
FIG. 1 illustrates a general reaction mechanism, comprising steps for synthesizing 2-substituted tetrahydrofuran derivatives and corresponding 2-substituted furan derivatives, according to synthesis methods described herein.

The figures are to be understood to present embodiments of the invention to aid in understanding of the principles and reaction chemistry involved, but not to limit the scope of the invention as defined in the appended claims. As would be apparent to one of skill in the art having knowledge of the present disclosure, synthesis methods according to various other embodiments of the invention will utilize particular reagents and reaction conditions determined, at least in part, according to specific objectives.

DETAILED DESCRIPTION OF EMBODIMENTS

As used herein, the term "substrate," or alternatively, "starting compound," refers to the initial compound that is subjected to one or preferably a series of conversion steps, such as "dehydrating," "cyclizing," and optional "oxidizing" conversion steps, to yield one or more cyclic products. These conversion steps do not preclude the use of prior conversion steps, such as under the same reaction conditions (e.g., in the same reactor) or under different reaction conditions (e.g., in a separate reactor), as used to produce the cyclic products. Such prior conversion steps can include the conversion of a readily available precursor, such as glucose, to gluconic acid or glucaric acid as the starting compound, such as by oxidation. Likewise, steps performed "to produce the 2-substituted furan derivative" do not preclude the use of subsequent conversion steps, such as under the same reaction conditions (e.g., in the same reactor) or under different reaction conditions (e.g., in a separate reactor), to obtain one or more other desired end products, such as by oxidation. For example, as described above, 5-(hydroxymethyl)furan-2-carboxylic acid may be oxidized to FDCA.

The terms "mol-%" and "wt-%" are used to designate amounts or concentrations in terms of percent by mole and percent by weight, respectively. Product yields given in terms of "mol-%" refer to the moles of a given intermediate or end product (e.g., 5-(hydroxymethyl)furan-2-carboxylic acid or FDCA) obtained, based on the moles of substrate used (introduced or fed to the reactor).

The term "alkyl," when used alone or in combination with other moieties, for example, when used in combination in "alkoxy," "alkoxyalkyl," "hydroxyalkyl," "carboxyalkyl," "alkanoyl," and "alkanoylalkyl," represents a hydrocarbon moiety that is derived from an alkane. When used alone, "alkyl" therefore includes "methyl" ($CH_3$—), "ethyl" ($C_2H_5$—), etc. When used in combination, the alkyl portion of the moiety "alkoxy" is bonded at an end of the moiety to the rest of the molecule, through an intervening oxygen linkage, —O—, such as in the case of "methoxy" ($CH_3$—O—), "ethoxy" ($C_2H_5$—O—), etc., which terms are encompassed by "alkoxy." The alkyl portion of the moiety "alkanoyl" is bonded at an end of the moiety to the rest of the molecule, through an intervening carbonyl linkage, —(C=O)—, with "methanoyl" (HC=O—) representing a terminal aldehyde moiety, "ethanoyl" ($CH_3$—(C=O)—), representing methyl bonded through a carbonyl linkage, etc., which terms are encompassed by "alkanoyl."

The term "hydroxy" represents the moiety —OH, and the term "carboxy" represents the moiety —(C=O)OH. The term "hydroxyalkyl" represents hydroxy bonded at the end of the moiety to the rest of the molecule, through an intervening divalent alkyl portion, such as in the case of "hydroxymethyl" (HO—$CH_2$—), "hydroxyethyl" (HO—$C_2H_5$—), etc., which terms are encompassed by "hydroxyalkyl." The term "carboxyalkyl" represents carboxy bonded at the end of the moiety to the rest of the molecule, through an intervening divalent alkyl portion, such as in the case of "carboxymethyl" (HO—(C=O)—$CH_2$—), "carboxyethyl" (HO—(C=O)—$C_2H_5$—), etc., which terms are encompassed by "carboxyalkyl." The term "alkoxyalkyl" includes both a terminal alkoxy portion (i.e., bonded at the end of the moiety), as defined above and indicated by the designation "alkoxy," as well as an intervening divalent alkyl portion, through which "alkoxy" is bonded to the rest of the molecule. Therefore, "alkoxyalkyl" encompasses "methoxymethyl" ($CH_3$—O—$CH_2$—), "methoxyethyl" ($CH_3$—O—$C_2H_4$—), "ethoxymethyl" ($C_2H_5$—O—$CH_2$—), "ethoxyethyl" ($C_2H_5$—O—$C_2H_4$—), etc. The term "alkanoylalkyl" includes both a terminal alkanoyl portion (i.e., bonded at the end of the moiety), as defined above and indicated by the designation "alkanoyl," as well as an intervening divalent alkyl portion, through which "alkanoyl" is bonded to the rest of the molecule. Therefore, "alkanoylalkyl" encompasses "methanoylmethyl" (H(C=O)—$CH_2$—), "methanoylethyl" (H(C=O)—$C_2H_4$—), "ethanoylmethyl" ($CH_3$—(C=O)—$CH_2$—), "ethanoylethyl" ($CH_3$—(C=O)—$C_2H_4$—), etc.

The term "optionally substituted" with respect to "alkyl," or with respect to either terminal or intervening alkyl portions of moieties as defined above, is meant to encompass the substitution of a hydrogen substituent at one or more carbon-hydrogen bonds of the alkyl or alkyl portion with the designated substituent. In the case of a substituent of hydroxy (—OH) or methyl (—$CH_3$), one, two, or three hydrogen substituents at carbon-hydrogen bonds of a terminal alkyl carbon atom may be substituted with respective —OH and/or —$CH_3$ substituents, and one or two hydrogen substituents at carbon-hydrogen bonds of an intervening (alkylene) alkyl carbon atom may be substituted with respective —OH and/or —$CH_3$ substituents. For example, in the case of a terminal alkyl portion, its terminal carbon atom may be substituted with two —$CH_3$ substituents, to yield a terminal isopropyl moiety, or may be substituted with three —$CH_3$ substituents, to yield a terminal t-butyl moiety. In the case of an intervening alkyl portion, or an intervening carbon atom of a terminal alkyl portion, one or two hydrogen substituents at carbon-hydrogen bonds of an alkylene carbon atom may be substituted with —CH₃ substituents to yield the corresponding methyl-substituted or dimethyl-substituted derivatives. From this description, analogous substitutions of a terminal alkyl carbon atom or intervening alkyl carbon atom with one or more —OH substituents can be appreciated. In the case of a substituent of carbonyl (=O), hydrogen substituents at two carbon-hydrogen bonds of either a terminal alkyl carbon atom or an intervening (alkylene) alkyl carbon atom may be substituted with =O, to yield a terminal aldehyde moiety (or group) or a carbonyl moiety (or group), respectively.

In view of the possible moieties and the manner in which they may be substituted, it is recognized that there may be overlap in moiety definitions, for example in the case of "methanoyl" and a terminal "methyl" being substituted with =O, both of which represent a terminal aldehyde moiety (or group). Specific moieties are mentioned, however, in order to emphasize their positive inclusion in a given compound. In addition, when "alkyl" or an "alkyl portion" is further defined with respect to its corresponding number of carbon atoms (e.g., alkyl or an alkyl portion "having from 1 to 5 carbon atoms"), optional —CH₃ substituents, when present, are not included in this number of carbon atoms. That is, the phrase "having from 1 to 5 carbon atoms," and other phrases defining the number of alkyl carbon atoms, refer to a backbone number of alkyl carbon atoms that may be further substituted with —CH₃ substituents or other substituents, according to the specific definitions given.

Carboxylic acid compounds include their corresponding salt forms. In the case of a starting compound or substrate bearing a carboxylic acid functional group, the salt form or the free acid form may be used in aqueous solution for carrying out the synthesis methods described herein. Corresponding salt forms of carboxylic acid include, for example, salts of alkali metals (e.g., the sodium salt form), salts of alkaline earth metals (e.g., the calcium salt form), and ammonium salts. Therefore, compounds such as "gluconic acid," "glucaric acid," etc. are meant to encompass salt forms of "gluconate," "glucarate," etc. Both generic and specific structures illustrating carboxylic acid compounds are likewise meant to encompass their salt forms or ionized forms, such that the structure of gluconic acid, for example, when shown with its carboxyl group un-ionized, is meant to encompass the structure with its carboxyl group ionized, and vice versa, with the un-ionized and ionized carboxyl group of the equivalent structures of this compound shown below:

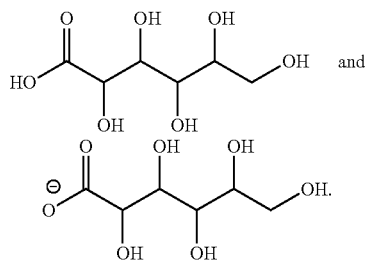

Compounds can possess one or more stereocenters, and structures are illustrated without regard for any specific stereochemistry, with the understanding that the reactions described with respect to substrates such as "gluconic acid," "glucaric acid," which according to their nomenclature designate a specific stereochemistry, may be likewise carried out in an analogous manner with the respective, non-stereo-specific substrates of "2,3,4,5,6-pentahydroxyhexanoic acid," "2,3,4,5-tetrahydroxyhexanedioic acid," as well as with all stereoisomers of such compounds. Therefore, unless otherwise specified, "gluconic acid" is intended to encompass "gluconic acid and stereoisomers thereof," as is intended with respect to other compounds designating a specific stereochemistry. Generic and specific compounds described herein may be used or obtained in the form of pure or purified (enriched) optical isomers or otherwise in the form of racemic mixtures thereof. The use of optically active substrates or starting compounds may result in the formation of optically active products, using the synthesis methods described herein, as would be appreciated by those having skill in the art, combined with knowledge from the present disclosure. If desired, the purification of a particular optical isomer, or enrichment in one optical isomer relative to another, can be obtained, for example, by the formation of diastereomeric salts through treatment with an optically active acid or base. Examples of appropriate acids are tartaric, diacetyltartaric, dibenzoyltartaric, ditoluoyltartaric and camphorsulfonic acid. Examples of appropriate bases are plant-derived chiral alkaloids. The mixtures of diastereomers are then separated by crystallization, followed by liberation of the optically active bases or acids from these salts. A different process for separation of optical isomers involves the use of a chiral chromatography column chosen to maximize the separation of the enantiomers. Still another available method involves synthesis of covalent diastereomeric molecules by reaction with an optically pure acid in an activated form or an optically pure isocyanate. The synthesized diastereomers can be separated by conventional means such as chromatography, distillation, crystallization or sublimation, and then hydrolyzed to yield the enantiomerically pure compound.

A general reaction mechanism for synthesizing 2-substituted furan derivatives is illustrated in FIG. 1. As shown, compound of general Formula I is a starting compound that is broadly an α-, β-dihydroxy carbonyl compound, which encompasses a preferred class of compounds, namely α-, β-dihydroxy carboxylates when $R^1$ is hydroxy (—OH) to provide a terminal carboxyl group on the left-hand side of the illustrated compound. A compound of the general Formula I in FIG. 1 comprises an α-hydroxy group, substituted at the α-carbon atom with respect to the carbonyl (C=O) group shown, as well as a β-hydroxy group, substituted at the (3-carbon atom with respect to this carbonyl group. In addition, this starting compound may further comprise a δ-hydroxy group, substituted at the δ-carbon atom, as well as an optional γ-hydroxy group, substituted at the γ-carbon atom. According to the illustrated synthesis mechanism, a first step of dehydration (water removal) causes removal of the β-hydroxy group, together with formation of a site of unsaturation, i.e., a carbon-carbon double bond between the α-carbon atom and the β-carbon atom. The resulting ethylenically unsaturated, dehydrated compound, shown as compound A, tends to maintain tautomeric equilibrium with the dicarbonyl intermediate shown as having general Formula IIA. The dehydrating step may therefore comprise forming water from a combination of the β-hydroxy group and hydrogen of the α-hydroxy group, in a starting compound or substrate of general Formula I.

The dicarbonyl intermediate compound of general Formula IIA may then undergo cyclization to ultimately produce the 2-substituted furan derivative of general Formula IIIB, in this case through an initial formation of a corresponding 2-substituted tetrahydrofuran derivative of Formula IIB, followed by dehydration of this compound. Consumption of the compound of general Formula IIB by its dehydration thereby drives the cyclization reaction forward, ultimately resulting in the further production of the dicarbonyl compound from compound A, by shifting the tautomeric equilibrium in this direction. The rate at which the 2-substituted tetrahydrofuran derivative becomes dehydrated may be regulated by the use of an optional dehydration catalyst, as well as reaction conditions, as described herein. In both the compounds of Formula IIB and IIIB, the oxygen ring member of the respective tetrahydrofuran and furan rings may be obtained from the γ-hydroxy group of the starting compound. In addition, according to the embodiment of FIG. 1, the 2-substituted furan derivative of general Formula IIIB is more particularly a 2,5-disubstituted furan derivative, having 2-, and 5-substituents, about the furan ring, of

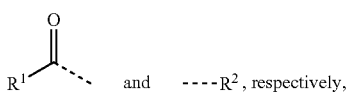

such that the 5-substituent is namely a substituent of the γ-carbon atom in the starting compound of Formula I, which does not undergo cyclization.

According to this synthesis method, 2-substituted furan derivatives may be produced from available 5- or 6-carbon atom-numbered, or higher carbon atom-numbered (e.g., 7-, 8-, 9- and/or 10-carbon atom-numbered) α-, β-dihydroxy carboxylates or carboxylic acids as starting compounds, such as 2,3,4,5-tetrahydroxypentanoic acid; 2,3,4-trihydroxy-5-oxopentanoic acid; 2,3,4-trihydroxypentanedioic acid; gluconic acid (or 2,3,4,5,6-pentahydroxyhexanoic acid generally); 2,3,4,5-tetrahydroxy-6-oxohexanoic acid, and glucaric acid (or 2,3,4,5-tetrahydroxyhexanedioic acid generally). Representative synthesis methods may therefore comprise converting available $C_5$-$C_{10}$ substrates, such as $C_5$-$C_6$ substrates that include readily available carbohydrates, to produce corresponding 2-substituted furan derivatives, as well as optional oxidized end products. In such embodiments, the number of carbon atoms of the starting compound may be preserved in the 2-substituted furan derivative, with the α-, β-, γ-, and δ-carbon atoms of this starting compound, together with the oxygen atom of the δ-hydroxy group, participating in ring formation and the remaining substituent of the δ-carbon atom manifesting as the 5-substituent about the furan ring. This 5-substituent, which therefore corresponds to $R^2$ in the compound of general Formula IIIB, may be oxidized, preferably in situ (i.e., in the case of a "one pot" process) for the sake of economy but possibly otherwise in a separate oxidation step.

With respect to compounds in FIG. 1 having the general Formulas I, IIA, IIB, and IIIB, as well as those having the general formula given for compound A, $R^1$ may be selected from the group consisting of alkyl, alkoxy, alkoxyalkyl, hydroxy, and hydroxyalkyl, wherein alkyl and the alkyl portions of alkoxy, alkoxyalkyl, and hydroxyalkyl have from 1 to 5 carbon atoms, optionally substituted with one or more substituents (i.e., may optionally have hydrogen substituents at carbon-hydrogen bonds substituted, as defined herein, with one or more substituents) selected from the group consisting of —OH, —$CH_3$, and =O. According to particular embodiments, in these respective compounds, including the starting compound of general Formula I, the dicarbonyl intermediate of general Formula IIA, the 2-substituted tetrahydrofuran derivative of general Formula IIB, and the 2-substituted furan derivative of general Formula IIIB, $R^1$ may be alkyl (e.g., having from 1 to 3 alkyl carbon atoms) and may result in a terminal ketone functional group in the respective compounds; $R^1$ may be alkoxy (e.g., having from 1 to 3 alkyl carbon atoms) and may result in a terminal ester functional group in the respective compounds; or $R^1$ may be hydroxy and may result in a terminal carboxyl functional group in the respective compounds. Preferably, $R^1$ is hydroxy, whereby the starting compound and the dicarbonyl intermediate are carboxylic acids. For example, as described above with respect to terms used herein generally, the starting compound, the dicarbonyl intermediate, the cyclization product(s) (e.g., substituted tetrahydrofuran or substituted furan), and/or the oxidized end product (e.g., FDCA) may be in the form of (e.g., present in the reaction mixture as) carboxylates, meaning compounds comprising a carboxylate anion and possibly present in salt form in an aqueous reaction mixture (e.g., in their corresponding ammonium salt form) that is used to carry out synthesis methods described herein. However, in some types of reaction mixtures that may be utilized, and particularly depending on the pH of such reaction mixture, these compounds may be present in their respective, free carboxylic acid forms.

With respect to compounds in FIG. 1 having the general Formulas I, IIA, IIB, and IIIB, as well as those having the general formula given for compound A, $R^2$ may be selected from the group consisting of a hydrogen substituent, alkyl, alkoxy, alkoxyalkyl, hydroxy, hydroxyalkyl, carboxy, carboxyalkyl, alkanoyl, and alkanoylalkyl, wherein alkyl and the alkyl portions of alkoxy, alkoxyalkyl, hydroxyalkyl, carboxyalkyl, alkanoyl, and alkanoylalkyl have from 1 to 5 carbon atoms, optionally substituted with one or more substituents selected from the group consisting of —OH, —$CH_3$, and =O. According to a particular embodiment, $R^2$ may selected from the group consisting of a hydrogen substituent, alkyl, alkoxy, hydroxy, hydroxyalkyl, carboxy, carboxyalkyl, alkanoyl, and alkanoylalkyl, wherein alkyl and the alkyl portions of alkoxy, alkoxyalkyl, hydroxyalkyl, carboxyalkyl, alkanoyl, and alkanoylalkyl have from 1 to 4 carbon atoms, optionally substituted with one or more of —OH and/or one or more of —$CH_3$. According to a more particular embodiment, $R^2$ may be a hydrogen substituent, alkyl, carboxy, carboxyalkyl, alkanoyl, or alkanoylalkyl, wherein alkyl and the alkyl portions of carboxyalkyl, alkanoyl, and alkanoylalkyl have from 1 to 3 carbons atoms, optionally substituted with one or more of —OH. Particular substrates having 5 or 6 carbon atoms include 2,3,4,5-tetrahydroxypentanoic acid; 2,3,4-trihydroxy-5-oxopentanoic acid; 2,3,4-trihydroxypentanedioic acid; gluconic acid (or 2,3,4,5,6-pentahydroxyhexanoic acid generally); 2,3,4,5-tetrahydroxy-6-oxohexanoic acid, and glucaric acid (or 2,3,4,5-tetrahydroxyhexanedioic acid generally).

Figure 2:
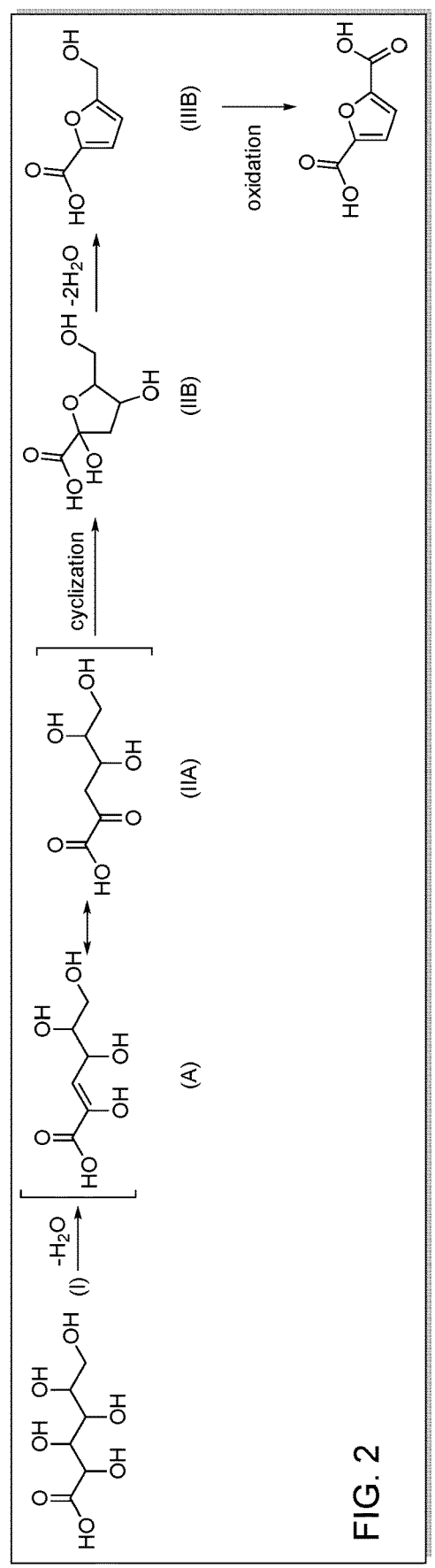
FIG. 2 illustrates a specific reaction mechanism, according to which gluconic acid is the starting material or substrate.

FIG. 2 illustrates the synthesis method presented in FIG. 1, using gluconic acid as a starting compound, or compound of Formula I, in which $R^2$ represents a substituent or moiety of hydroxymethyl,

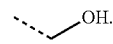

In this embodiment, the dicarbonyl intermediate of Formula IIA is 2-keto-3-deoxygluconic acid (2-keto-4,5,6-trihydroxyhexanoic acid), as shown. This dicarbonyl intermediate can then undergo cyclization to yield the 2-substituted tetrahydrofuran derivative of Formula IIB, which in the embodiment illustrated in FIG. 2 is namely 2,4-dihydroxy-5-(hydroxymethyl)tetrahydrofuran-2-carboxylic acid. Dehydration then yields the 2-substituted furan derivative of Formula IIIB, which is namely the 2,5-substituted furan derivative, 5-(hydroxymethyl)furan-2-carboxylic acid. Oxidation of this compound, as shown in FIG. 2, produces furandicarboxylic acid (FDCA). As noted above, oxidation to form FDCA may be carried out under reaction conditions described herein, for synthesis of the 2-subsituted furan derivative of Formula IIIB generally. According to preferred embodiments, therefore, with respect to this compound shown in FIG. 1, $R^1$ may be hydroxy and $R^2$ may be carboxy or hydroxymethyl. In the particular case of $R^1$ being hydroxy and $R^2$ being hydroxymethyl, the starting compound is gluconic acid and the 2,5-disubstituted furan derivative is 5-(hydroxymethyl)furan-2-carboxylic acid. The method may further comprise oxidizing at least a portion of the 5-(hydroxymethyl)furan-2-carboxylic acid to produce FDCA.

Representative methods are therefore described herein, for synthesizing a 2-substituted furan derivative, having the same number of carbon atoms relative to an α-, β-dihydroxy carboxylate starting compound. The methods comprise reacting this starting compound in a reaction mixture, preferably an aqueous reaction mixture, which may comprise a dehydration catalyst, i.e., a catalyst or promoter of the reaction step shown in FIGS. 1 and 2 as the conversion of the compound of general Formula IIB to the compound of general Formula IIIB. Preferred dehydration catalysts comprise one or more dehydration active metals, such as tungsten, molybdenum, and/or vanadium, which may be present in the form of corresponding salts in the reaction mixture, such as tungstate, molybdate, or vanadate salts, which include a metatungstate salt, a paratungstate salt, a metamolybdate salt, a paramolybdate salt, a metavanadate salt, or a paravanadate salt. Representative tungstate salts are salts of Group 1 (alkali) metals or Group 2 (alkaline earth) metals, as well as ammonium salts. Ammonium metatungstate and ammonium paratungstate salts are representative. A dehydration catalyst (e.g., ammonium metatungstate) may be present in the reaction mixture in an amount of from about 0.1 mol-% to about 30 mol-%, from about 0.5 mol-% to about 10 mol-%, or from about 1 mol-% to about 5 mol-%, relative to the number of moles of substrate, for example according to the initial reactor loading composition in the case of a batchwise reaction or according to a steady-state composition in the case of a continuous reaction. The dehydration catalyst may also, or may alternatively, be present in the reaction mixture in an amount such that the moles of dehydration active metal (e.g., tungsten, molybdenum, or vanadium) may represent from about 6 mol-% to about 50 mol-%, or from about 10 mol-% to about 35 mol-%, relative to the number of moles of substrate. Other dehydration catalysts can include solid acids and/or Lewis acids (e.g., organometallic compounds, including organotin compounds).

According to representative methods, the end product FDCA may be produced from a combination of dehydration and oxidation of the compound of general Formula JIB. The reaction mixture may include a base, such as ammonium hydroxide or otherwise an alkali or alkaline earth metal hydroxide (e.g., lithium hydroxide, sodium hydroxide, potassium hydroxide, etc.), and the starting compound and compounds having general Formulas I, IIA, IIB, and IIIB may be present in the reaction mixture in the form of their respective carboxylate salt forms (e.g., ammonium carboxylate forms) in the case of $R^1$ being hydroxy (—OH). Otherwise, these compounds may be present in their free acid forms, for example in the case of an aqueous reaction mixture that is neutral or acidic. In representative embodiments, the reaction mixture may have a pH of about 6.5 or less (e.g., from about 2 to about 6.5, or from about 3 to about 6), such as by virtue of comprising an organic acid or inorganic acid.

Particular methods are directed to the synthesis of FDCA from an α-, β-dihydroxy carboxylate starting compound having 6 carbon atoms, such as a salt of gluconate (or 2,3,4,5,6-pentahydroxyhexanoate generally); 2,3,4,5-tetrahydroxy-6-oxohexanoate; or glucarate (or 2,3,4,5-tetrahydroxyhexanedioate generally). As noted above, these starting compounds may also be present in their free acid form, i.e., as gluconic acid (or 2,3,4,5,6-pentahydroxyhexanoic acid generally); 2,3,4,5-tetrahydroxy-6-oxohexanoic acid; or glucaric acid (or 2,3,4,5-tetrahydroxyhexanedioic acid generally), depending on the pH of the reaction mixture. As described herein, representative methods comprise dehydrating this starting compound to form a dicarbonyl intermediate by transformation of the alpha hydroxy group to a second carbonyl group and removal of the beta hydroxy group, and cyclizing this dicarbonyl intermediate by forming a furan ring comprising, as ring members, the α- through δ-carbon atoms of the dicarbonyl intermediate, corresponding to the α- through δ-carbon atoms with respect to the carboxylate group of the starting compound, to form the FDCA or a precursor of the FDCA. The precursor may, for example, be 5-(hydroxymethyl)furan-2-carboxylic acid that may be oxidized, in an optional oxidizing step, to produce the FDCA.

According to particular embodiments the total yield of the 2,5-substituted furan derivative having general Formula IIIB, or its oxidized end product (e.g., FDCA) (depending on whether the reaction environment is sufficiently oxidizing), based on the theoretical yields proceeding through the respective pathways as also described herein, may be generally at least about 25 mol-% (e.g., from about 25 mol-% to about 90 mol-%), typically at least about 35 mol-% (e.g., from about 35 mol-% to about 80 mol-%), and often at least about 50 mol-% (e.g., from about 50 mol-% to about 75 mol-%).

The reaction mixture, which is preferably an aqueous reaction mixture, may further comprise a solid, heterogeneous catalyst, such as solid particulate catalyst for catalyzing any of the steps of (i) dehydration of the substrate, (ii) cyclization of the dicarbonyl intermediate, (iii) dehydration of the 2-substituted tetrahydrofuran derivative, and/or (iv) oxidation of the 2-substituted furan derivative, as described herein. A representative solid catalyst may comprise, as a catalytically active component, one or more transition metals selected from Groups 8-11 of the Periodic Table, such as, for example, ruthenium (Ru), cobalt (Co), nickel (Ni), platinum (Pt), palladium (Pd), or gold (Au). A preferred transition metal is ruthenium. The catalyst may further comprise a solid support of the transition metal(s), with the metals being dispersed on the solid support according to a distribution, for example preferentially near the outer surface of the solid support or otherwise substantially uniformly throughout a porous solid support, depending on the particular catalyst preparation technique used (e.g., evaporative impregnation of a solution of the active metal). Preferably, the active metal, or such metals in combination, is/are present in an amount from about 0.1 wt-% to about 15 wt-%, or from about 0.5 wt-% to about 10 wt-%, based on the total weight of the solid catalyst.

The active metal(s) of the solid catalyst may be present in the reaction mixture in an amount such that the moles of active metal(s) (e.g., ruthenium) represent from about 0.1 mol-% to about 15 mol-%, or from about 0.5 mol-% to about 10 mol-%, relative to the number of moles of substrate, for example according to the initial reactor loading composition in the case of a batchwise reaction or according to steady-state composition in the case of a continuous reaction. The solid support is preferably refractory in the reaction mixture and under the synthesis reaction conditions described herein. Representative solid supports comprise one or more metal oxides, such as aluminum oxide (alumina), silicon oxide (silica), titanium oxide (titania), zirconium oxide (zirconia), magnesium oxide (magnesia), strontium oxide (strontia), etc. A preferred solid support is carbon. According to a particular embodiment, the solid catalyst comprises ruthenium on a carbon support, with the ruthenium being present in an amount within a range given above, based on total catalyst weight and/or within a range given above, relative to the number of moles of substrate.

A typical reaction environment associated with the synthesis of a 2-substituted tetrahydrofuran derivative and/or 2-substituted furan derivative, according to methods described herein, includes an inert or possibly oxidizing atmosphere. The reaction may be carried out, for example, under dehydration/cyclization reaction conditions that include an absolute pressure from about 0.1 megapascals (MPa) (14.5 psi) to about 2 MPa (290 psi), such as from about 0.1 MPa (14.5 psi) to about 0.5 MPa (73 psi), obtained by atmospheric blanketing or pressurization with a suitable gas, for example, nitrogen, nitrogen-enriched air, or air.

Other dehydration/cyclization reaction conditions may include a temperature generally from about 0° C. to about 250° C., typically from about 20° C. to about 150° C., and often from about 40° C. to about 100° C. The reaction time, i.e., time at which the reaction mixture is maintained under conditions of pressure and temperature at any target values or target sub-ranges within any of the ranges of pressure and temperature given above (e.g., a target, total pressure value of 0.25 MPa (36 psi) and a target temperature of 50° C.), is from about 0.5 hours to about 24 hours, and preferably from about 1 hour to about 5 hours, in the case of a batchwise reaction. For a continuous reaction, these reaction times correspond to reactor residence times. Continuous operation may be performed, for example, under the conditions of pressure and temperature described above, with continuous feeding of the substrate and continuous withdrawal of the reaction mixture comprising the 2-substituted tetrahydrofuran derivative and/or 2-substituted furan derivative. Continuous operation may further include the continuous purification of the derivative(s), the continuous separation of process streams comprising unconverted gaseous and/or liquid products, and/or the continuous recycle of one or more of such process streams back to the reaction mixture, maintained in the synthesis reactor. In the case of recycle operation, the yields of the 2-substituted tetrahydrofuran derivative and/or 2-substituted furan derivative, as described above, will correspond to the "once-through" or "per-pass" yield, with higher overall yields being possible due to the recycle.

Overall, aspects of the invention relate to the use of synthesis methods described herein to produce 2-substituted furan derivatives and/or oxidized, 2-substituted furan derivative end product(s), and particularly FDCA, from readily available, or easily derived, substrates. The end product(s) may be produced from oxidation either in situ or in a further, separate reaction stage. The 2-substituted furan derivatives and/or end product(s) have the same number of carbon atoms, relative to the substrates used to produce these products. The methods may advantageously address various shortcomings of conventional methods. Those having skill in the art, with the knowledge gained from the present disclosure, will recognize that various changes can be made to these processes in attaining these and other advantages, without departing from the scope of the present disclosure. As such, it should be understood that the features of the disclosure are susceptible to modifications and/or substitutions without departing from the scope of this disclosure. The specific embodiments illustrated and described herein are for illustrative purposes only, and not limiting of the invention as set forth in the appended claims.

What is claimed is:

1. A method for synthesizing a 2-substituted furan derivative, the method comprising:
    (a) dehydrating a starting compound comprising an alpha hydroxy group, substituted at an alpha carbon atom with respect to a first carbonyl group, and a beta hydroxy group, substituted at a beta carbon atom with respect to the first carbonyl group, to form a dicarbonyl intermediate by transformation of the alpha hydroxy group to a second carbonyl group and removal of the beta hydroxy group;
    (b) cyclizing the dicarbonyl intermediate to produce the 2-substituted furan derivative comprising a 2-substituent of a furan ring including the first carbonyl group, wherein the method is carried out non-enzymatically, and further wherein the starting compound is a salt of gluconic acid or a salt of glucaric acid.

2. The method of claim 1, wherein the dehydrating comprises forming water from a combination of the beta hydroxy group and hydrogen of the alpha hydroxy group.

3. The method of claim 1, wherein step (b) comprises, prior to forming the 2-substituted furan derivative, forming a 2-substituted tetrahydrofuran derivative comprising the 2-substituent and dehydrating the 2-substituted tetrahydrofuran derivative to the 2-substituted furan derivative.

4. The method of claim 1, wherein the 2-substituted furan derivative is a 2,5-disubstituted furan derivative, having both a 2-substituent and a 5-substitutent about the furan ring of the 2,5-disubstituted furan derivative.

5. The method of claim 4, wherein the 2,5-disubstituted furan derivative has, as the 5-substituent, a substituent of a delta carbon atom of the starting compound that does not cyclize.

6. The method of claim 5, wherein the 2,5-disubstituted furan derivative is a corresponding salt of 5-(hydroxymethyl)furan-2-carboxylic acid.

7. The method of claim 6, further comprising oxidizing at least a portion of the salt of 5-(hydroxymethyl)furan-2-carboxylic acid to provide a corresponding salt of furan-2, 5-dicarboxylic acid.

8. The method of claim 7, wherein the oxidizing is carried out in a same reaction vessel as used for the dehydrating and cyclizing.

9. The method of claim 1,
    wherein the dehydrating and cyclizing steps are carried out under an inert environment and at a temperature of at least about 30° C.

10. The method of claim 9, wherein the dehydrating and cyclizing steps are carried out in the presence of a dehydration catalyst comprising a dehydration active metal.

11. The method of claim 10, wherein the dehydration active metal is tungsten, molybdenum, or vanadium.

12. The method of claim 11, wherein the tungsten, molybdenum, or vanadium is present in the form of its respective tungstate, molybdate, or vanadate salt.

13. The method of claim 10, wherein the dehydration catalyst is present in the reaction mixture in an amount from about 0.1 mol-% to about 30 mol-%, based on the $\alpha$-, $\beta$-dihydroxy carbonyl compound.

14. A method of synthesizing furan-2,5-dicarboxylic acid, the method comprising:
  (a) dehydrating an $\alpha$-, $\beta$-dihydroxy carboxylate starting material in the form of a salt of gluconic acid or glucaric acid to form a dicarbonyl intermediate from oxidation of the alpha hydroxy group of the starting material to a carbonyl group and removal of the beta hydroxy group of the starting material;
  (b) cyclizing the dicarbonyl intermediate by forming a furan ring comprising, as ring members, alpha through delta carbon atoms of the dicarbonyl intermediate, corresponding to alpha through delta carbon atoms with respect to the carboxylate group of the starting compound, to form the corresponding salt of furan-2,5-dicarboxylic acid or the corresponding salt of a precursor of the furan-2,5-dicarboxylic acid;
  (c) optionally oxidizing the corresponding salt of the precursor of the furan-2,5-dicarboxylic acid to form the salt of furan-2,5-dicarboxylic acid; and
  (d) converting the salt of furan-2,5-dicarboxylic acid from step (b) and step (c) if performed to furan-2,5-dicarboxylic acid, by acidulation;
wherein the method is carried out non-enzymatically.

15. The method of claim 14, wherein the precursor is 5-(hydroxymethyl)furan-2-carboxylic acid.

16. The method of claim 14, wherein salts of both gluconic acid and glucaric acid are present as staring materials and are dehydrated and cyclized together.

17. The method of claim 16, wherein the dehydrating and cyclizing steps are carried out in the presence of a dehydration catalyst comprising a dehydration active metal, and further comprising the step of filtering out the catalyst following the dehydrating and cyclizing steps.

* * * * *